(12) United States Patent
Sugita (10) Patent No.: US 8,480,670 B2
(45) Date of Patent: Jul. 9, 2013

(54) BIPOLAR HIGH-FREQUENCY TREATMENT TOOL FOR ENDOSCOPE

(75) Inventor: Noriyuki Sugita, Saitama (JP)

(73) Assignee: Hoya Corporation, Tokyo (JP)

( * ) Notice: Subject to any disclaimer, the term of this patent is extended or adjusted under 35 U.S.C. 154(b) by 1401 days.

(21) Appl. No.: 11/675,754

(22) Filed: Feb. 16, 2007

(65) Prior Publication Data

US 2007/0198011 A1     Aug. 23, 2007

(30) Foreign Application Priority Data

Feb. 20, 2006  (JP) ................................. 2006-041905

(51) Int. Cl.
*A61B 18/14*   (2006.01)

(52) U.S. Cl.
USPC .............................................. 606/50; 606/46

(58) Field of Classification Search
USPC ....................................... 606/50–52
See application file for complete search history.

(56) References Cited

U.S. PATENT DOCUMENTS

| | | | |
|---|---|---|---|
| 6,015,381 A | | 1/2000 | Ouchi |
| 6,951,560 B1 * | | 10/2005 | Kidooka ........................ 606/51 |
| 7,326,209 B2 | | 2/2008 | Kidooka |
| 2002/0115996 A1 * | | 8/2002 | Wilson et al. ................... 606/46 |
| 2004/0019352 A1 | | 1/2004 | Kidooka |
| 2004/0220565 A1 * | | 11/2004 | Bales et al. ..................... 606/47 |
| 2006/0155271 A1 | | 7/2006 | Sugita et al. |
| 2006/0178669 A1 | | 8/2006 | Sugita et al. |

FOREIGN PATENT DOCUMENTS

| | | |
|---|---|---|
| JP | 10-192286 | 7/1998 |
| JP | 2004-057454 | 2/2004 |
| JP | 2005-296304 | 10/2005 |

OTHER PUBLICATIONS

Japanese Office Action dated Oct. 22, 2009 that issued with respect to patent family member Japanese Patent Application No. 2006-041905.
English Language Abstract of JP 2005-296304.
U.S. Appl. No. 11/550,528 to Sugita, filed Oct. 18, 2006.
U.S. Appl. No. 11/550,508 to Sugita, filed Oct. 18, 2006.
U.S. Appl. No. 11/678,169 to Sugita, filed Feb. 23, 2007.

* cited by examiner

*Primary Examiner* — Michael Peffley
*Assistant Examiner* — Samantha Good
(74) *Attorney, Agent, or Firm* — Greenblum & Bernstein P.L.C.

(57) ABSTRACT

A bipolar high-frequency treatment tool for an endoscope comprising a flexible sheath having a multi-lumen tube which is rotatable about an axis of the flexible sheath and is formed to have a pair of guide lumens, a pair of high-frequency electrodes which are arranged to be movable at a tip end of the flexible sheath and are adapted to be electrically insulated from each other, a pair of operating wires which are made of an electrically conductive material but are adapted to be electrically insulated from each other, wherein each of the pair of operating wires is respectively arranged in each of the guide lumens, and wherein the pair of high-frequency electrodes is rotated as the pair of operating wires is rotated and as the multi-lumen tube is rotated about the axis of the flexible sheath accordingly, is provided.

4 Claims, 9 Drawing Sheets

BIPOLAR HIGH-FREQUENCY TREATMENT TOOL FOR ENDOSCOPE

BACKGROUND OF THE INVENTION

The present invention relates to a bipolar high-frequency treatment tool for an endoscope having a pair of high-frequency electrodes which are electrically insulated from each other at a tip end of a flexible sheath of the endoscope.

Generally, an endoscope unit having a bipolar high-frequency treatment tool is provided with a pair of high-frequency electrodes which are electrically insulated from each other at a tip end of a flexible sheath. In such an endoscope, a pair of operation wires to operate the electrodes is arranged to extend in parallel with an axis of the sheath throughout an entire length of the sheath. The pair of operation wires are configured to be advanced forward and retracted backward and are made of an electrically conductive material to conduct electrical currents respectively to the high-frequency electrodes although each of the operation wires are maintained insulated. Examples of such an endoscope unit are disclosed in Japanese Patent Provisional Publication Nos. 2004-57454 and 2005-296304.

In the endoscope units disclosed in the above-references publications, when treatment using high-frequency currents is performed, it is often desired that an orientation of the electrodes with respect to a treatment object is adjusted by rotating the electrodes about an axis of the flexible sheath. In such a case, conventionally, the flexible sheath together with the electrodes is rotated about the axis of the flexible sheath at a proximal end thereof by an operator.

With this operation, however, as the flexible sheath is inserted into an insertion channel of the endoscope which is winding inside a human body, resistance applied to the sheath against inner surfaces of the insertion channel is not constant throughout the length of the sheath and may vary. Therefore, in many cases, a distal end portion of sheath may be rapidly rotated even when a proximal end portion of the sheath is rotated slowly, and vice versa, and in other words, the flexible sheath are often rotated partially and irregularly. Thus, it has been difficult to adjust the orientation of the high-frequency electrodes with respect to the axis of the flexible sheath.

SUMMARY OF THE INVENTION

In view of the foregoing drawbacks, the present invention is advantageous in that a bipolar high-frequency treatment tool for an endoscope having a pair of high-frequency electrodes of which an orientation with respect to an axis of a flexible sheath can be easily adjusted is achieved.

According to an aspect of the present invention, a bipolar high-frequency treatment tool for an endoscope is provided. The bipolar high-frequency treatment tool includes a flexible sheath having a multi-lumen tube which is adapted to be rotatable about an axis of the flexible sheath and is formed to have a pair of guide lumens extending in an axial direction of the flexible sheath throughout an entire length of the flexible sheath, a pair of high-frequency electrodes which are arranged to be movable at a tip end of the flexible sheath and are adapted to be electrically insulated from each other, a pair of operating wires which are made of an electrically conductive material to conduct high-frequency electric current from a power source to the pair of high-frequency electrodes but are adapted to be electrically insulated from each other. Each of the pair of operating wires is respectively arranged in each of the guide lumens, and the pair of high-frequency electrodes is rotated about the axis of the flexible sheath as the pair of operating wires is rotated about the axis of the flexible sheath by a rotating force applied to proximal portions of the operating wires and as the multi-lumen tube is rotated about the axis of the flexible sheath inside the flexible sheath accordingly.

Optionally, each of the pair of operating wires may be arranged to be movable in the axial direction of the flexible sheath inside each of the pair of guide lumens of the multi-lumen tube.

Optionally, the flexible sheath may be provided with an operating unit at a proximal end thereof, the operating unit being rotatable about the axis of the flexible sheath with respect to a rotatable member which is attached to interconnect the operating unit and the flexible sheath. The proximal portions of the operating wires extending from a proximal end of the multi-lumen tube may be fixed to the operating unit so that the proximal portions of the operating wires are rotated integrally with the operating unit as the operating unit is rotated about the axis of the flexible sheath with respect to the rotatable member.

Optionally, the proximal portions of the pair of operating wires extending from the proximal end of the multi-lumen tube may be provided with enhancing covers respectively.

Optionally, at least one of the pair of operating wires may be coated with an electrically insulating coating material at a portion that extends from a distal end of the multi-lumen tube to one of the bipolar high-frequency electrodes.

Optionally, each of the pair of operating wires may be configured with a core wire and a plurality of peripheral wires which are twisted around the core wire. Solely the core wire of the at least one of the pair of operating wires is coated with the electrically insulating coating material and the plurality of peripheral wires are removed from the at least one of the pair of operating wires in the portion in which the at least one of the pair of operating wires is coated with the electrically insulating coating material.

Optionally, the flexible sheath may be provided with a frame to hold the high-frequency electrodes at the tip end thereof. The frame may be adapted to be rotatable integrally with the pair of high-frequency electrodes with respect to the flexible sheath about the axis of the flexible sheath when the high-frequency electrodes are rotated by the rotating force applied to the proximal portions of the operating wires.

Optionally, the pair of high-frequency electrodes may be adapted to be protrusible and retractable from the tip end of the flexible sheath. The multi-lumen tube may be formed to be shorter than the length of the flexible sheath for an amount which is equivalent to an amount of the high-frequency electrodes to be retracted inside the flexible sheath.

DETAILED DESCRIPTION OF THE EMBODIMENTS

Hereinafter, referring to the accompanying drawings, according to illustrative embodiments of the invention will be described.

First Embodiment

Figure 1:
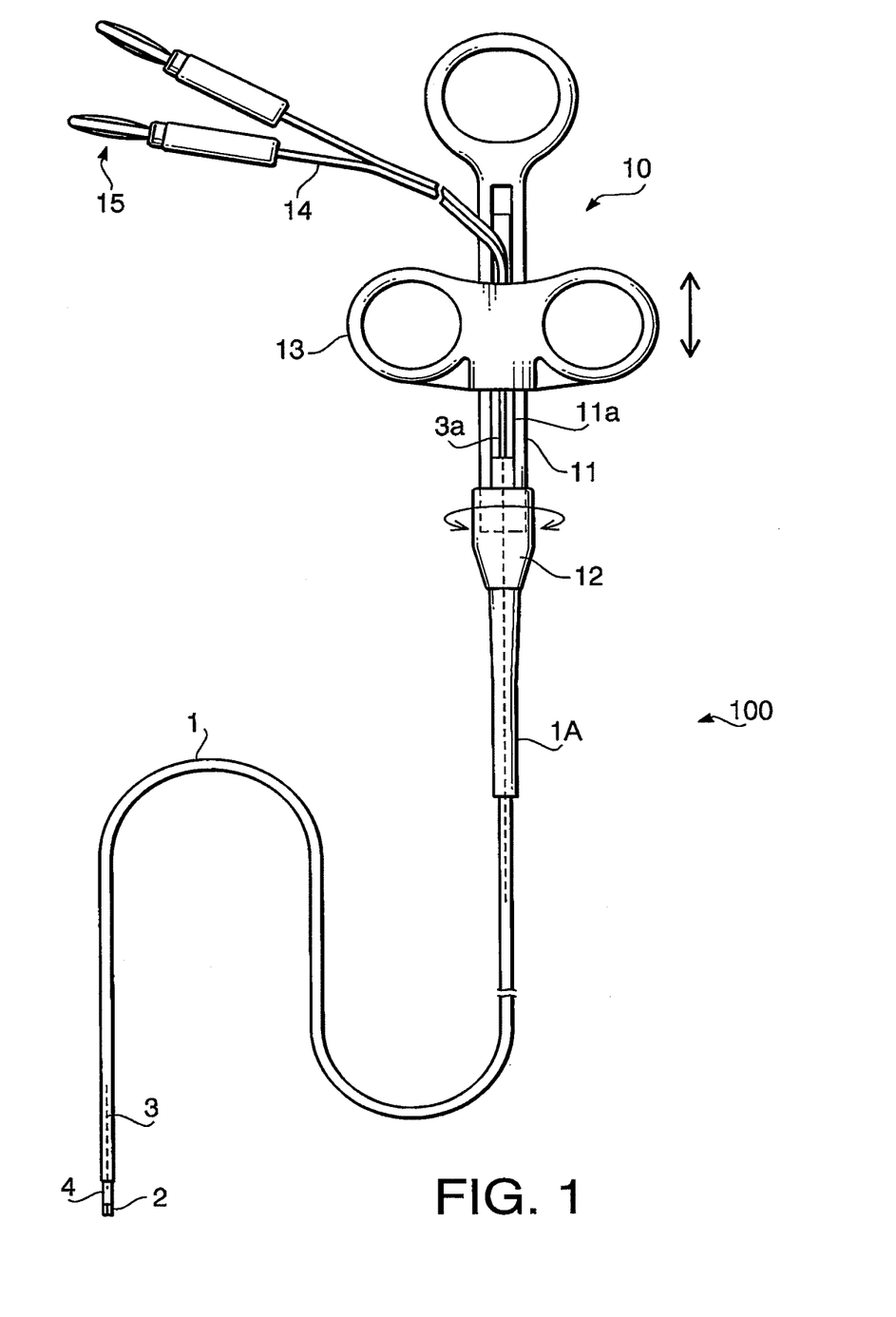
FIG. 1 illustrates an entire configuration of a bipolar high-frequency treatment tool for an endoscope with high-frequency electrodes according to a first embodiment of the invention.
Figure 2:
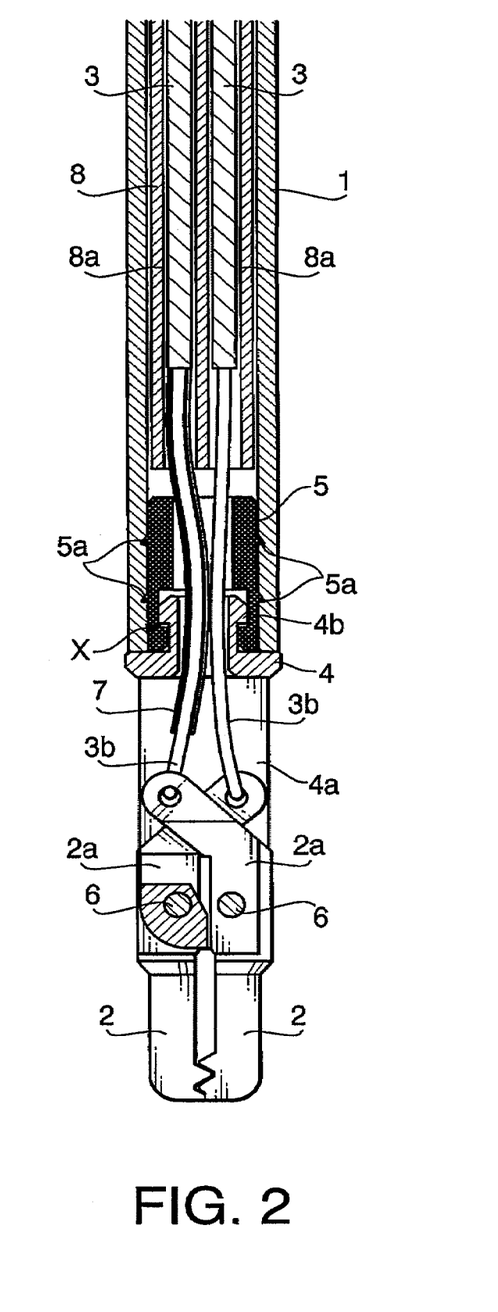
FIG. 2 is a cross-sectional side view of the bipolar high-frequency treatment tool for the endoscope with the high-frequency electrodes thereof being closed according to the first embodiment of the invention.
Figure 3:
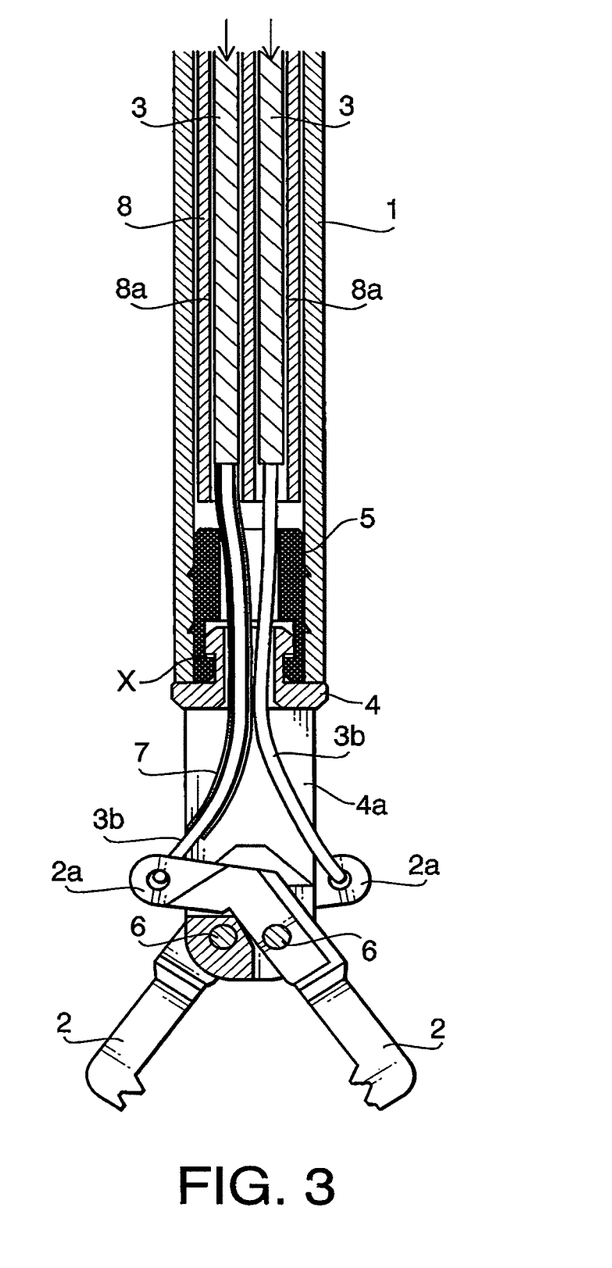
FIG. 3 is a cross-sectional side view of the bipolar high-frequency treatment tool for the endoscope with the high-frequency electrodes thereof being open according to the first embodiment of the invention.

FIG. 1 illustrates an entire configuration of a bipolar high-frequency treatment tool 100 for an endoscope with high-frequency electrodes according to a first embodiment of the invention. FIG. 2 is a cross-sectional side view of the bipolar high-frequency treatment tool 100 with the high-frequency electrodes thereof being closed according to the first embodiment of the invention. FIG. 3 is a cross-sectional side view of the bipolar high-frequency treatment tool 100 with the high-frequency electrodes thereof being open according to the first embodiment of the invention. As shown in FIGS. 2 and 3, the bipolar high-frequency treatment tool 100 is provided with a pair of high-frequency electrodes 2, which is configured to open and close by operations to a pair of operating wires 3, and the high-frequency electrodes 2 are supported by a supporting frame 4 which is arranged at a tip-end portion of a flexible sheath 1. In the flexible sheath 1, the pair of operating wires 3 are arranged in parallel with each other and with an axis of the flexible sheath 1. Distal ends of the operating wires 3 are respectively connected to the high-frequency electrodes 2.

As shown in FIG. 1, the flexible sheath 1 is connected with an operating unit 10 at a proximal end thereof. The operating unit 10 includes a shaft portion 11 having a slit 11a, which is formed in parallel with an axis of the shaft portion 11. The shaft portion 11 is attached to an annular rotatable member 12, which can be rotated about the axis of the shaft portion 11, and the annular rotatable member 12 is fixed to the proximal end of the flexible sheath. The bipolar high-frequency treatment tool 100 is further provided with a protector tube 1A, which covers around the proximal portion of the flexible sheath 1 to protect the flexible sheath 1 from being forcibly bent.

The operating wires 3 are exposed from the slit 11a of the shaft portion 11 at proximal portions 3a thereof and are fixed to slider handle 13, which is slidably attached to the shaft portion 11. The proximal portions 3a of the operating wires 3 are respectively connected to conductors 14, which extend outward of the operating unit 10 through the slider handle 13. Distal ends of the conductors 14 are connected to power supply plugs 15 respectively.

With the above configuration, the pair of the high-frequency electrodes 2, which are a positive pole and a negative pole, are connected to a high-frequency power supplying unit (not shown) via the operating wires 3 and the power supply plugs 15, and the high-frequency electrodes 2 are arbitrarily opened and closed via the operating wires 3 by sliding operations to the slider handle 13 along the shaft portion 11.

As an operation using the bipolar high-frequency treatment tool 100 is performed, the flexible sheath 1 is inserted into an insertion channel of the endoscope (not shown). The flexible sheath 1 is a flexible tube having smooth surfaces made of an electrically insulating material such as polytetrafluoroethylene.

The flexible sheath 1 is further provided with a tubular supporting tube 5 as a distal end thereof. The supporting tube 5 is pressed fit inside the flexible sheath 1 at a position wherein a distal end thereof aligns to the distal end of the flexible sheath 1. The supporting tube 5 is provided with a plurality of protrusions 5a which protrude outward from an outer surface of the supporting tube 5 to wedge into the inner surface of the flexible sheath 1.

The supporting frame 4 is made of an electrically insulating material and is formed to have a smaller diameter portion 4b at a proximal portion thereof. The smaller diameter portion 4b is inserted into and engaged with the supporting tube 5 as an engaging portion X. In the engaging portion X, an inner diameter of the supporting tube 5 is formed to be different from the other portion of the supporting tube 5, while an outer diameter of the supporting frame 4 is formed to be different from the other portion of the supporting frame 4 correspondingly to the inner diameter of the supporting tube 5 so that the supporting frame 4 is rotatably engaged to the supporting tube 5 at the engaging portion X with respect to the axis of the supporting tube 5 (i.e., the axis of the flexible tube 1) but is restricted from moving in the axial direction.

Each of the high-frequency electrodes 2 is formed to have an arm 2a. The arms 2a are arranged inside a slit 4a, which is formed in the supporting frame 4, and are rotatably held by shafts 6 which traverse inside the slit 4a so that the high-frequency electrodes 2 are insulated from each other and are rotated to open and close about the shaft 6 respectively toward a front of the high-frequency electrodes 2.

Inside the flexible sheath 1, a flexible multi-lumen tube 8 having smooth surfaces made of an electrically insulating material such as polytetrafluoroethylene is included. The multi-lumen tube 8 is formed to have a pair of guide lumens 8a which extend in parallel with the axis of the flexible sheath 1 and is arranged inside the entire length of the flexible sheath 1. An outer diameter of the multi-lumen tube 8 is configured to loosely fit inside the flexible sheath 1 so that the multi-lumen tube 8 can be rotated inside the flexible sheath 1 about the axis of the flexible sheath 1. Further, it should be noted that the multi-lumen tube 8 is restricted from moving beyond the supporting tube 5 by the supporting tube 5.

The guide lumens 8a are formed for example in symmetry positions in a cross-section of the multi-lumen tube 8 with respect to the axis of the multi-lumen 8. Each of the operating wires 3 is arranged inside one of the guide lumens 8a respectively.

Thus, the operating wires are electrically insulated from each other by the multi-lumen tube 8. Outer diameters of the operating wires 3 are configured to loosely fit in diameters of the guide lumens 8a so that the operating wires 3 can be advanced and retracted inside the guide lumens 8a in the axial direction.

In the present embodiment, the operating wires 3 are configured with a core wire 3b and a plurality of stainless conductive thin wires which are twisted around the core wire. In portions of the operating wires 3 that extend outward (i.e., toward a lower side in FIG. 2) from the guide lumens 8a, solely the core wires are extended, and the other thin wires are removed from the operating wires 3.

The remaining core wires of the operating wires 3 extend through the supporting tube 5 to be connected with proximal portions of the arms 2a of the high-frequency electrodes 2 respectively. It should be noted that at least one of the core wires extending from the guide lumens 8a is coated with an insulating cover 7 so that the operating wires 3 can be prevented from being electrically conducted to each other.

In the above configuration, as shown in FIG. 3, as the operating wires 3 are advanced toward the distal end thereof from the proximal portions which are connected to the operating unit 10, the high-frequency electrodes 2 are opened in a similar movement to a pair of pincers accordingly. Thus, the treatment object can be nipped between the high-frequency electrodes 2, and the high-frequency treatment can be performed as the high-frequency electrodes 2 are conducted.

Figure 4:
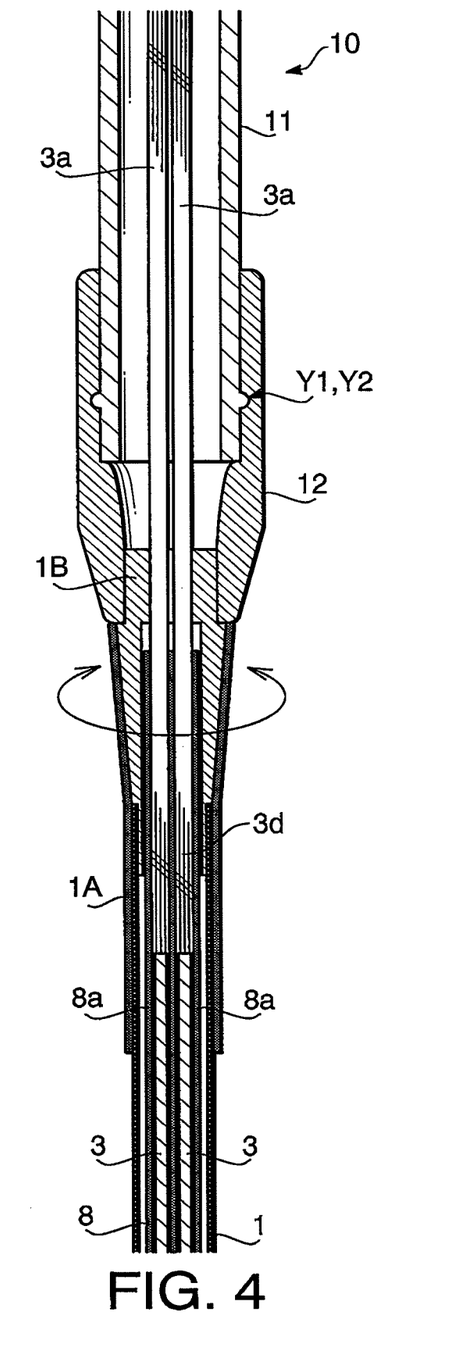
FIG. 4 is a cross-sectional side view of a connecting portion of a flexible sheath and an operating unit of the bipolar high-frequency treatment tool according to the first embodiment of the invention.

FIG. 4 is a cross-sectional side view of a connecting portion of the flexible sheath 1 and the operating unit 10 of the bipolar high-frequency treatment tool 100 according to the first embodiment of the invention. As shown in FIG. 4, the flexible sheath 1 includes a connecting member 1B, which is fixed to the proximal end of the flexible sheath 1. The connecting member 1B is further fixed to the annular rotatable member 12 so that the annular rotatable member 12 can be rotated integrally with the flexible sheath 1 with respect to the shaft portion 11.

It should be noted that the shaft portion 11 is formed to have an annular protrusion Y1 on an outer surface thereof, and the annular rotatable member 12 is formed to have an annular groove Y2. As the annular protrusion Y1 and the annular groove Y2 engage with each other, the annular rotatable member 12 is prevented from moving in the axial direction with respect to the shaft portion 11.

The proximal end of the multi-lumen tube 8 extends in vicinity of the proximal end of the flexible sheath 1. A proximal portion of the connecting member 1B is formed to have an inner diameter which is smaller than the outer diameter of the multi-lumen tube 8 so that the multi-lumen tube 8 is prevented from being moved beyond the connecting member 1B toward the proximal end of the bipolar high-frequency treatment tool 100.

The operating wires 3 include proximal portions 3a respectively, which are portions extending from the guide lumens 8a toward the operating unit 10. The proximal portions 3a are covered by enhancing pipes 3d which prevent the operating wires 3 from being conducted to each other.

In the bipolar high-frequency treatment tool 100 in the above configuration, the proximal portions 3a of the operating wires 3 are rotated together with the operating unit 10 as one of the protector tube 1A and the annular rotatable member 12 is held by the operator and the entire operating unit 10 is rotated about the axis of the shaft 11.

Accordingly, the multi-lumen tube 8 with the operating wires 3 inserted therethrough is rotated inside the flexible sheath 1 so that the rotation is conveyed to the distal portion of the multi-lumen tube 8 smoothly. It should be noted that in a configuration wherein the operating wires are directly arranged inside the flexible sheath 1, the operating wires 3 are twisted with each other and the rotation is not properly conveyed.

Figure 5:
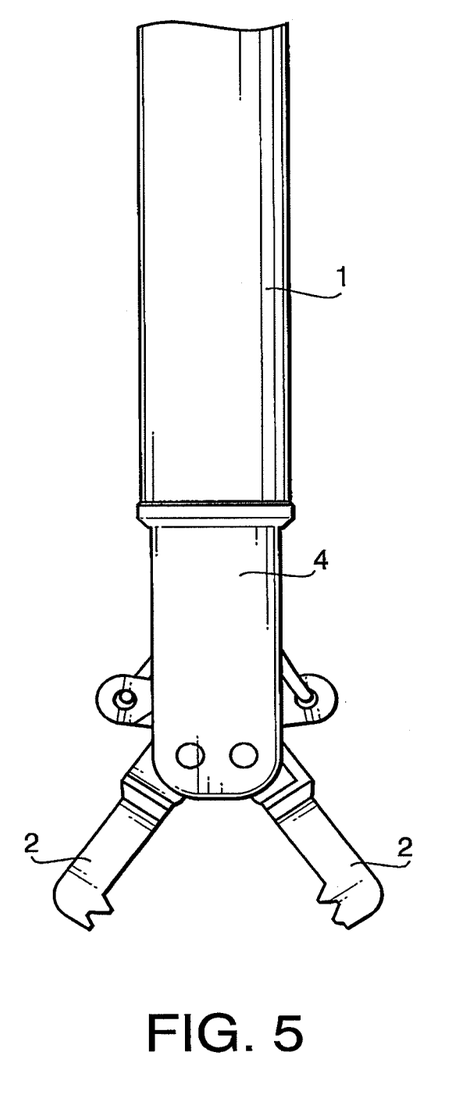
FIG. 5 is a side view of the bipolar high-frequency treatment tool for the endoscope with high-frequency electrodes thereof being open according to the first embodiment of the invention.
Figure 6:
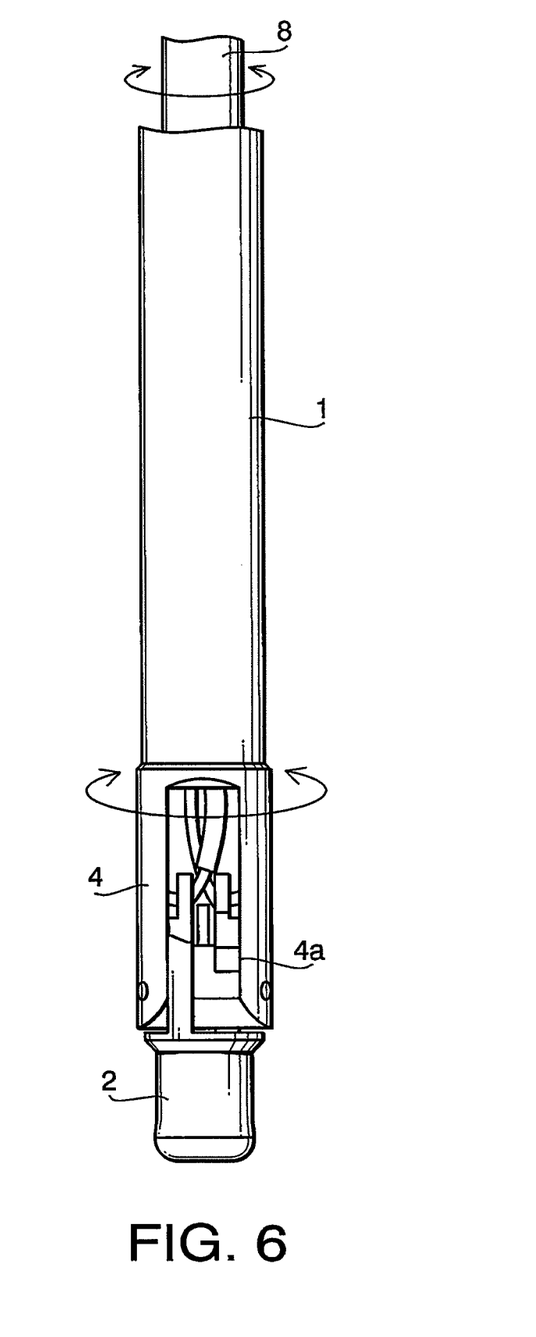
FIG. 6 is a side view of the bipolar high-frequency treatment tool for the endoscope with high-frequency electrodes thereof being open and rotated according to the first embodiment of the invention.

The rotation of the multi-lumen tube 8 about the axis of the flexible sheath 1 is conveyed to the supporting frame 4 via the operating wires 3 and the arms 2a. FIG. 5 is a side view of the bipolar high-frequency treatment tool 100 with the high-frequency electrodes 2 being open according to the first embodiment of the invention. FIG. 6 is a side view of the bipolar high-frequency treatment tool 100 with high-frequency electrodes 2 being open and rotated according to the first embodiment of the invention. As shown in FIGS. 5 and 6, the supporting frame 4 is rotated about the axis of the flexible sheath 1 at the tip end of the flexible sheath 1, and the high-frequency electrodes 2 are rotated smoothly about the axis of the flexible sheath 1 accordingly. Therefore, the orientation of the high-frequency electrodes 2 at the tip end of the flexible sheath 1 can be smoothly adjusted as desired by a remote operation.

Second Embodiment

Figure 7:
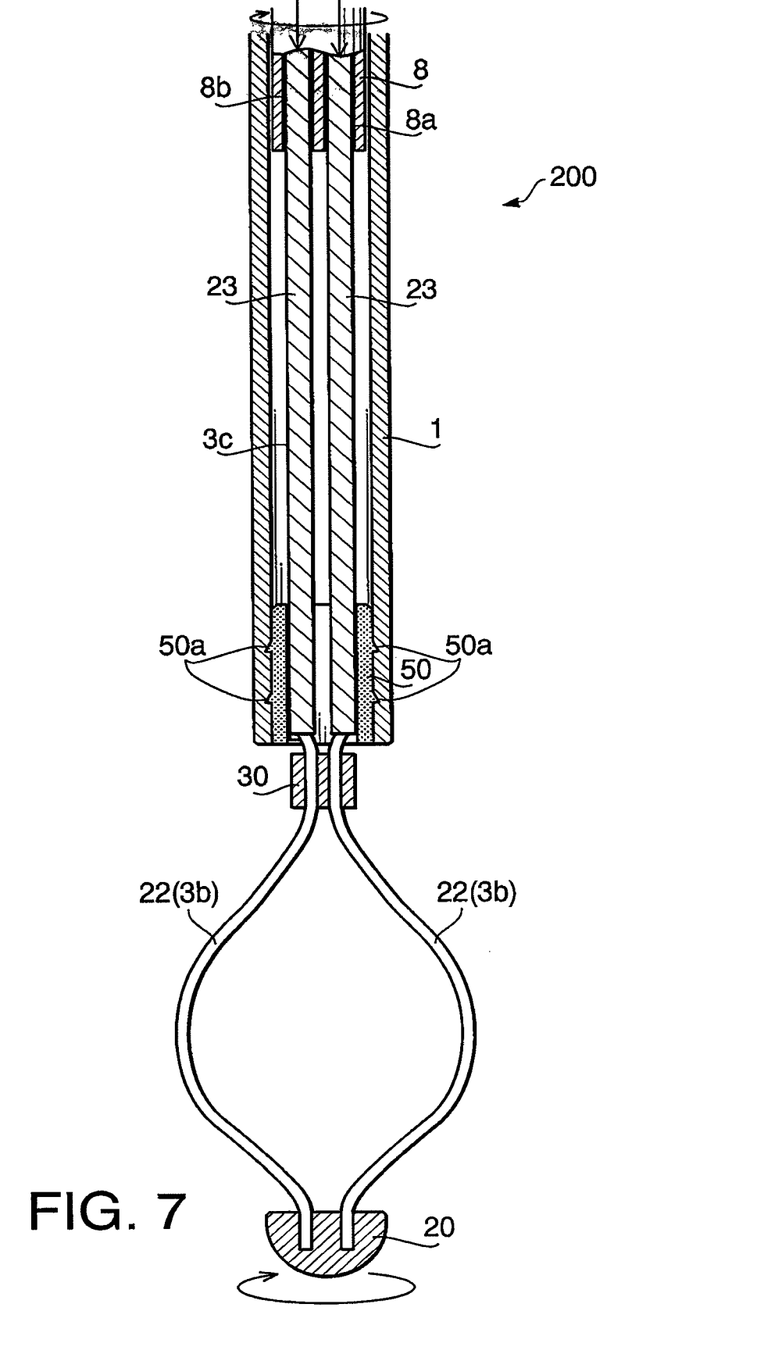
FIG. 7 is a cross-sectional side view of a bipolar high-frequency treatment tool for an endoscope with high-frequency electrodes thereof being protruded outward according to a second embodiment of the invention.

FIG. 7 is a cross-sectional side view of a bipolar high-frequency treatment tool 200 for an endoscope with high-frequency electrodes thereof being protruded outward according to a second embodiment of the invention. In the second embodiment, the bipolar high-frequency treatment tool 200 is configured to be a high-frequency snare, and components arranged at the tip end portion of the flexible sheath 1 are different from the configuration of the bipolar high-frequency treatment tool 100 of the first embodiment. In the second embodiment, a configuration similar to that of the first embodiment is referred to by an identical reference numeral and description of that will be omitted. In the tip end portion of the flexible sheath 1, a stopper tube 50 which prevents the multi-lumen tube 8 from being advanced therebeyond is pressed (inserted) to be fixed. Further, protrusions 50a to wedge into the inner surface of the flexible sheath 1 are formed on an outer surface of the stopper tube 50.

A pair of high-frequency electrodes 22 are curved to form a loop and are configured with core wires 3b extending from the operating wires 23. The high-frequency electrodes 22 are provided with an electrically insulting distal chip 20 and a proximal chip 30 at a distal end thereof and a proximal end thereof respectively so that the high-frequency electrodes 22 can be prevented from becoming in contact with each other. It should be noted that the distal chip 20 also serves as a stopper to prevent the high-frequency electrodes 22 from being entirely withdrawn in the flexible sheath 1.

Figure 8:
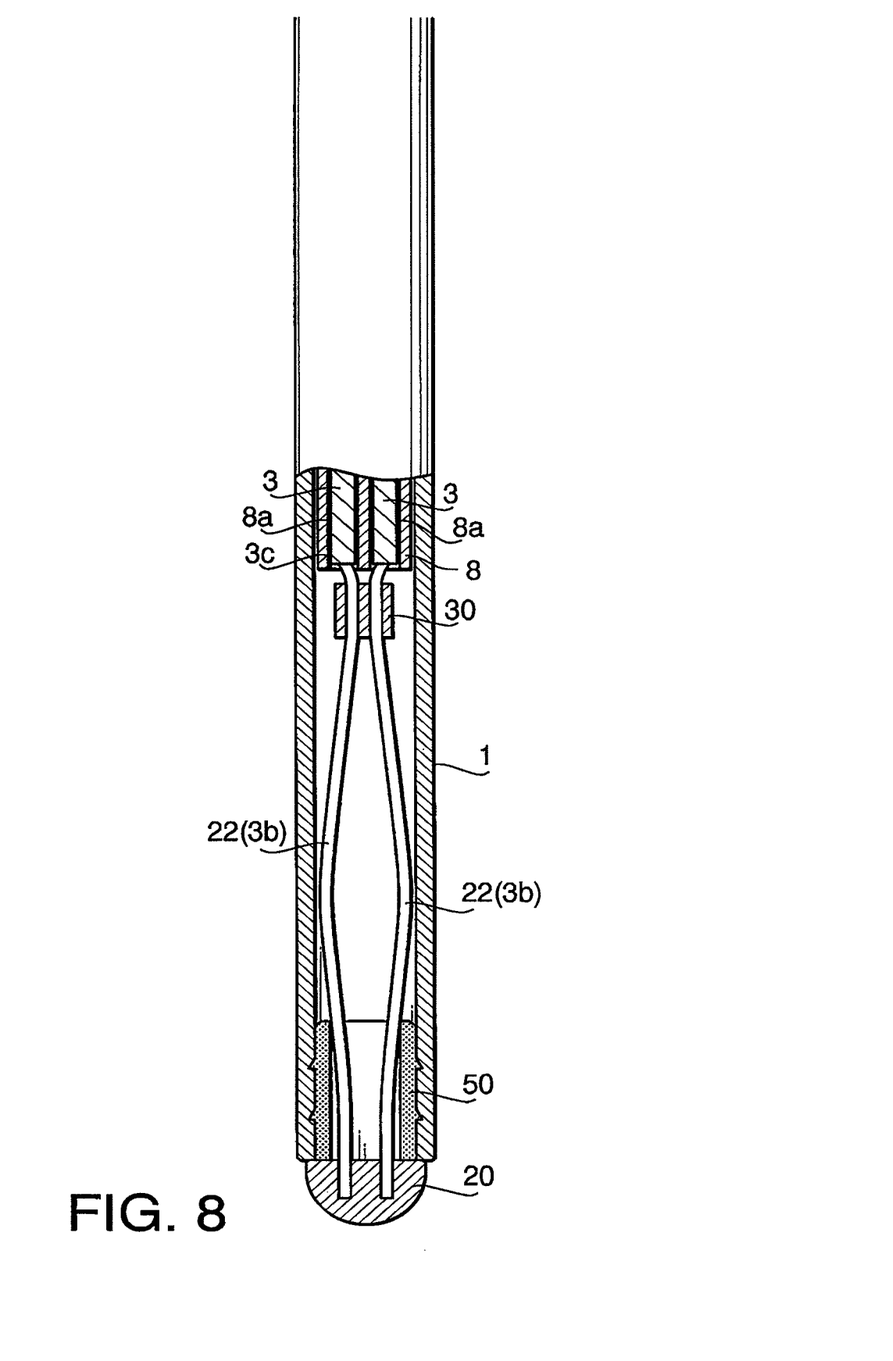
FIG. 8 is a cross-sectional side view of the bipolar high-frequency treatment tool for the endoscope with high-frequency electrodes thereof being retracted inward according to the second embodiment of the invention.

FIG. 8 is a cross-sectional side view of the bipolar high-frequency treatment tool 200 with high-frequency electrodes 22 being retracted inward according to the second embodiment of the invention. The high-frequency electrodes 22 are resiliently deformed to be substantially straightened so that the high-frequency electrodes 22 are retracted inside the flexible sheath 1 as the operating wires 23 are retracted toward the operating unit 10 as shown in FIG. 8. On the other hand, the high-frequency electrodes 22 are advanced outward and recover to form the curved loop as the operating wires 23 are advanced forward toward the distal end of the high-frequency electrodes 22 as shown in FIG. 7.

The multi-lumen tube 8 is formed to be shorter for a length corresponding to an amount that the high-frequency electrodes 22 are retracted inside the flexible sheath 1. At least one of the high-frequency electrodes 22 is coated with an electrically insulating cover 3c so that the high-frequency electrodes 22 are prevented from being conducted with each other when the high-frequency electrodes 22 are retracted in the flexible sheath 1 and the high-frequency electrodes 22 become in contact with each other therein.

With the above configuration, the rotation of the operating unit 10 with respect to the flexible sheath 1 about the axis thereof can be conveyed to the high-frequency electrodes 22 via the multi-lumen tube 8, and the high-frequency electrodes 22 are rotated smoothly about the axis of the flexible sheath 1. Accordingly, the orientation of the high-frequency electrodes 22 at the tip end of the flexible sheath 1 can be smoothly adjusted as desired by an remote operation.

Although examples of carrying out the invention have been described, those skilled in the art will appreciate that there are numerous variations and permutations of the bipolar high-frequency treatment tool that falls within the spirit and scope of the invention as set forth in the appended claims. It is to be understood that the subject matter defined in the appended claims is not necessarily limited to the specific features or act described above. Rather, the specific features and acts described above are disclosed as example forms of implementing the claims.

Figure 9:
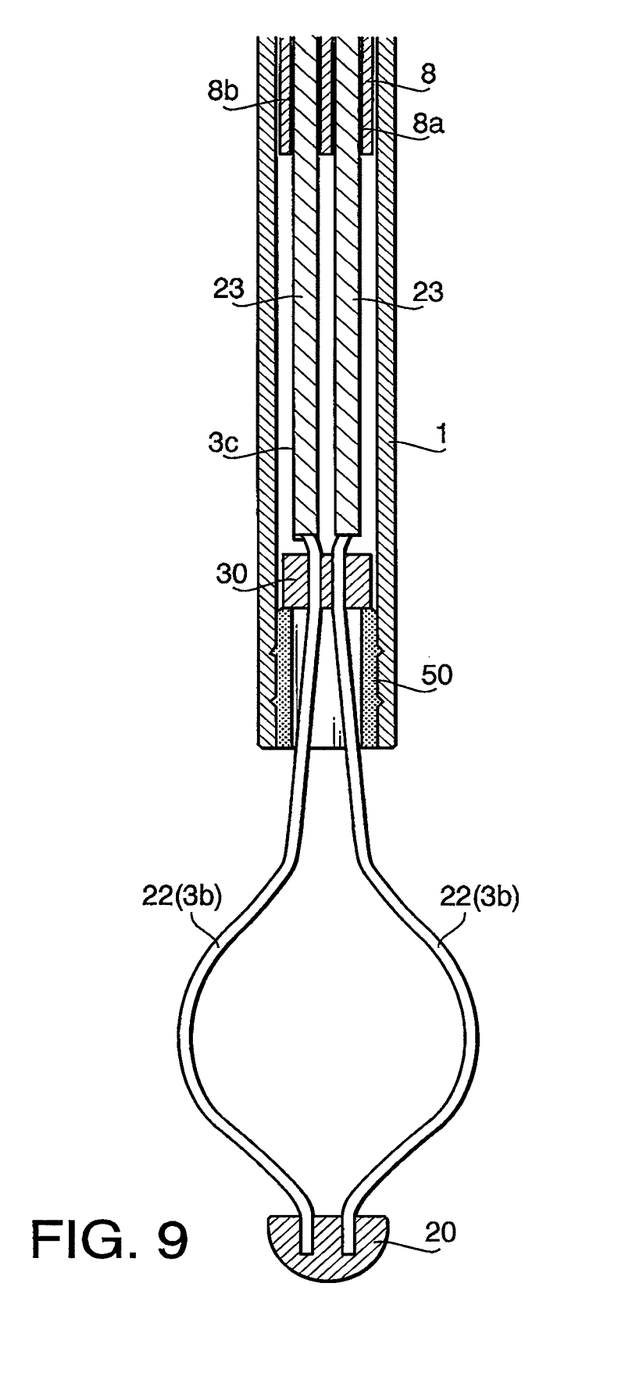
FIG. 9 is a cross-sectional side view of a bipolar high-frequency treatment tool for an endoscope with high-frequency electrodes thereof being protruded outward according to a third embodiment of the invention.

For example, as shown in FIG. 9, the proximal tip 30 may be configured to become in contact with the stopper tube 50 inside the flexible sheath 1. With this configuration, a length of the high-frequency electrodes 22 to be protruded outward from the distal end of the flexible sheath 1 can be more specifically restricted. Further, as the proximal chip 30 is pressed against the stopper tube 50, the rotation of the operating wires 23 about the axis of the flexible sheath 1 can be restrained so that the high-frequency electrodes 22 can be stably paused in the position.

The present disclosure relates to the subject matter contained in Japanese Patent Application No. P2006-041905, filed on Feb. 20, 2006, which is expressly incorporated herein by reference in its entirety.

What is claimed is:

1. A bipolar high-frequency treatment tool for an endoscope, comprising;
   a flexible sheath;
   a multi-lumen tube that is separate from and positioned within the flexible sheath, the multi-lumen tube being rotatable relative to the flexible sheath and about an axis of the flexible sheath, and the multi lumen tube is formed having two guide lumens extending in an axial direction of the flexible sheath throughout an entire length of the flexible sheath;
   two high-frequency electrodes which are arranged to be movable at a tip end of the flexible sheath and are electrically insulated from each other;
   two operating wires which are made of an electrically conductive material to conduct high-frequency electric current from a power source to the two high-frequency electrodes, the operating wires being electrically insulated from each other,
   an operating unit fixed to the proximal portions of the operating wires and having a shaft portion; and
   a rotatable member configured to be rotatable relative to the shaft portion of the operating unit and about the axis of the shaft portion of the operating unit, the rotatable member being fixed to the proximal end of the flexible sheath,
   wherein each of the two operating wires is positioned within a corresponding one of the guide lumens, and is arranged to be movable in the axial direction of the flexible sheath,
   wherein the rotatable member is not movable in an axial direction with respect to the shaft portion of the operating unit,
   wherein at least one of the two operating wires is coated with an electrically insulating coating material at a portion that extends from a distal end of the multi-lumen tube to one of the two high-frequency electrodes,
   wherein each of the two operating wires is configured with a core wire and a plurality of peripheral wires which are twisted around the core wire, and
   wherein solely the core wire of the at least one of the two operating wires is coated with the electrically insulating coating material and the plurality of peripheral wires are removed from the core wire of the at least one of the two operating wires in the portion in which the at least one of the two operating wires is coated with the electrically insulating coating material.

2. The bipolar high-frequency treatment tool according to claim 1, wherein the proximal portions of the operating wires extending from the proximal end of the multi-lumen tube are provided with enhancing covers respectively.

3. The bipolar high-frequency treatment tool according to claim 1,
   wherein the flexible sheath is provided with a frame to hold the high-frequency electrodes at the tip end thereof, and
   wherein the frame is adapted to be rotatable integrally with the high-frequency electrodes with respect to the flexible sheath about the axis of the flexible sheath when the high-frequency electrodes are rotated by the rotating force applied to the proximal portions of the operating wires.

4. The bipolar high-frequency treatment tool according to claim 1, wherein the high-frequency electrodes are adapted to be protrusible and retractable from the tip end of the flexible sheath, and
   wherein the multi-lumen tube is formed to be shorter than the length of the flexible sheath for an amount which is equivalent to an amount of the high-frequency electrodes to be retracted inside the flexible sheath.

* * * * *